United States Patent [19]

Drago

[11] Patent Number: 5,283,261
[45] Date of Patent: Feb. 1, 1994

[54] USE OF NIMESULIDE N THE TREATMENT OF CATARACT

[75] Inventor: Filippo Drago, Milan, Italy

[73] Assignee: LPB Istituto Farmaceutico, Milan, Italy

[21] Appl. No.: 951,405

[22] Filed: Sep. 25, 1992

[30] Foreign Application Priority Data

Sep. 20, 1991 [IT] Italy ............................ MI91A002509

[51] Int. Cl.$^5$ .............................................. A61K 31/18
[52] U.S. Cl. ..................................... 514/605; 514/601; 514/912
[58] Field of Search ......................... 514/601, 605, 912

[56] References Cited

PUBLICATIONS

The Merck Index, Eleventh Edition, 1989, p. 1035.

Primary Examiner—Zohreh A. Fay
Attorney, Agent, or Firm—Mathews, Woodbridge & Collins

[57] ABSTRACT

Nimesulide is effective in the treatment of cataracts.

3 Claims, No Drawings

USE OF NIMESULIDE N THE TREATMENT OF CATARACT

The present invention to the use of N-(4-nitro-2-phenoxyphenyl)methanesulfonamide for the treatment of cataract.

Cataract is known to be caused by changes in the physical and chemical properties of the proteins of the crystalline lens, with a consequent opacification of the latter. Recently, free radicals and inflammatory processes were also recognized to play a role in cataract pathogenesis.

Although in therapeutical practice a large number of medicaments which are capable of inhibiting the inflammatory processes and the formation of free radicals are known and used for the treatment of other pathologies, only few of said medicaments proved to be somehow useful for the treatment of cataract.

Therefore, the need exists for a wider choice of medicaments for use in cataract pathology, which increasingly occurs, mainly in the Western Countries, also due to the longer mean life.

Now it has surprisingly been found, and it is the object of the present invention, that N-(-4-nitro-2-phenoxyphenyl)methanesulfonamide of formula (I):

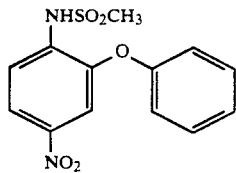

also known under the name nimesulide, which is an antiinflammatory medicament having a peculiar mechanism of action, characterized by a discrepancy between the anti-inflammatory potency and the inhibition of prostaglandin synthetase in vitro, has a marked activity as an anticataract agent, and therefore it can advantageously be used for the treatment of such a pathology.

Particularly, nimesulide turned out to be capable of inhibiting the protein denaturation and the development of the crystalline lens opacification, to an equal or higher extent than bendazac lysine, which is a known anticataract agent.

A further object of the present invention is provided by pharmaceutical compositions for the treatment of cataract, containing nimesulide as the active ingredient.

The pharmacological tests carried out with the compound of the invention are described hereinbelow.

Nimesulide was dissolved in dimethylsulfoxide (DMSO) at concentration 100 folds higher than those to be tested, and subsequent dilutions were carried out in an equilibrated Hanks saline, without phenol red. An equivalent amount of DMSO was added as the control.

Depolymerization of hyaluronic acid was studied as described by Schmut et al. (1987). The kinematic viscosity of hyaluronic acid was measured using a KPG-Ubbelhode viscosimeter at 20° C., and the mean values of 3 observations were evaluated in cSt. The viscosity measurement was effected before and 16 hours after the addition of 0,5 um/ml of Na-ascorbate, pH 7,5. Nimesulide ($1\times10^{-4}$M, $5\times10^{-4}$M) was added in a test before the addition of Na-ascorbate.

The effect of nimesulide on albumin polymerization was studied as described previously (Catanese et al., 1976): bovine serum-albumin was heated to 58° C. for 4 hours. Before and after heating, an electrophoresis on polyacrylamide gel was carried out. Nimesulide was added at the same doses in a test before heating.

Rat crystalline lenses, immediately after the operation, were incubated in a medium containing glucose (5,55 mill) in 15% foetal calf serum. After 4 day incubation, an opacity was observed due to the protein denaturation. The protein concentration and composition in the lenses were measured by electrophoresis on polyacrylamide gel before and after the addition of nimesulide ($1\times10^{-4}$M, $5\times10^{4}$M).

In all the tests, a clinically active anticataract agent, i.e. bendazac lysine, was used in equimolecular concentrations.

The addition of Na-ascorbate induced a decrease in hyaluronic acid viscosity, thus evidencing the depolymerization of this substance. Nimesulide seemed to inhibit such a depolymerization. The lower concentration turned out to be inactive from this respect. Moreover, albumin heating in the control tests caused 6 polymers to form, starting from albumin monomer. The potency of this effect showed no differences for the two concentrations.

The electrophoretic analysis of the lens proteins before the induction of cataract revealed the presence of 4 protein groups, of similar molecular weights. 15 Polymers were found to be present in cataract. Surprisingly, nimesulide was found to inhibit the formation of cataract, moreover it prevented the formation of polymers of the lens proteins.

In all the tests, bendazac equimolar amounts were found to be effective. Nimesulide turned out to be more potent than bendazac in inhibiting denaturation of the rat lens proteins.

It should be pointed out that nimesulide inhibited the protein denaturation and the development of opacity in rat crystalline lens.

The inhibition of hyaluronic acid depolymerization and of the heating-induced protein denaturation by bendazac are known. The results of the capability of bendazac to prevent cataract in rat lens are known and described (Catanese et al. 1976).

Nimesulide turned out to be as potent as bendazac in all the effected tests.

TABLE 1

| Effect of nimesulide and bendazac on kinematic viscosity (in cSt) of a hyaluronic acid solution after addition of Na-ascorbate. | |
|---|---|
| Hyaluronic acid (basal) | 3.0 |
| Hyaluronic acid + Na-ascorbate | 2.0 |
| Hyaluronic acid + nimesulide ($1\times10^{-4}$) + Na-ascorbate | 2.0 |
| Hyaluronic acid + nimesulide ($5\times10^{-4}$) + Na-ascorbate | 2.8 |
| Hyaluronic acid + bendazac ($1\times10^{-4}$) + Na-ascorbate | 2.6 |
| Hyaluronic acid + bendazac ($5\times10^{-4}$) + Na-ascorbate | 2.8 |

Mean of 3 observations. MSE was omitted for amounts lower than 0.1

TABLE 2

| Effect of nimesulide and bendazac on the denaturation of albumin monomer induced by heating. | | |
|---|---|---|
| | | polymers |
| Control | | 78 |
| nimesulide | ($1\times10^{-4}$) | 32 |
| | ($5\times10^{-4}$) | 30 |
| bendazac | ($1\times10^{-4}$) | 56 |

TABLE 2-continued

Effect of nimesulide and bendazac on the denaturation of albumin monomer induced by heating.

| | polymers |
|---|---|
| $(5 \times 10^{-4})$ | 40 |

The values are expressed as % polymer concentration on the total concentration of the albumin monomer.

TABLE 3

Effect of nimesulide and bendazac on the denaturation of the rat lens proteins.

| | | polymers |
|---|---|---|
| Control | | 67 |
| nimesulide | $(1 \times 10^{-4})$ | 35 |
| | $(5 \times 10^{-4})$ | 32 |
| bendazac | $(1 \times 10^{-4})$ | 36 |
| | $(5 \times 10^{-4})$ | 30 |

The values are expressed as % polymer concentration on the total protein concentration in a normal crystalline lens.

What stated above clearly shows that nimesulide can be used for the treatment of cataract. For the envisaged therapeutical uses, nimesulide can be used by the oral or topical routes, in form of ophthalmic formulations. In case of oral administration, the mean daily dosages can range from 50 to 500 mg, possibly divided in more administrations. Topical ophthalmic formulations, such as eye drops, ointments and the like, can contain the active ingredient in concentrations from 0,01 to 1%. The preparation of the pharmaceutical formulations can be carried out according to conventional techniques and excipients, such as those described in "Remington's Pharmaceutical Sciences Handbook", Mack Publ. Co., N.Y., U.S.A.

I claim:

1. A method for treating cataracts in a patient in need thereof which comprises administering an effective amount of nimesulide.

2. The method according to claim 1 wherein the nimesulide is administered orally.

3. The method according to claim 1 wherein the nimesulide is administered topically.

* * * * *